United States Patent [19]

Sakamoto et al.

[11] Patent Number: 4,985,460
[45] Date of Patent: * Jan. 15, 1991

[54] BENZOYLUREA DERIVATIVE AND ITS PRODUCTION AND USE

[75] Inventors: Noriyasu Sakamoto, Nishinomiya; Tatsuya Mori, Toyonaka; Tadashi Ohsumi, Nishinomiya; Toshihiko Yano, Ashiya; Izumi Fujimoto, Minoo; Yoji Takada, Toyonaka, all of Japan

[73] Assignee: Sumitomo Chemical Company, Limited, Osaka, Japan

[ * ] Notice: The portion of the term of this patent subsequent to Feb. 27, 2007 has been disclaimed.

[21] Appl. No.: 386,159

[22] Filed: Jul. 28, 1989

Related U.S. Application Data

[63] Continuation-in-part of Ser. No. 150,990, Feb. 1, 1988, Pat. No. 4,904,696.

[30] Foreign Application Priority Data

Feb. 4, 1987 [JP] Japan .................................. 62-23975
Aug. 27, 1987 [JP] Japan .................................. 62-213945

[51] Int. Cl.$^5$ .............................................. A01N 9/12
[52] U.S. Cl. .................................................... 514/594
[58] Field of Search ........................... 564/44; 514/594

[56] References Cited

U.S. PATENT DOCUMENTS

| | | |
|---|---|---|
| 3,989,842 | 11/1976 | Wellenga et al. |
| 4,139,636 | 2/1979 | Sirrenberg et al. |
| 4,170,657 | 10/1979 | Rigterink. |
| 4,457,943 | 7/1984 | Becker et al. |
| 4,904,696 | 2/1990 | Sakemoto et al. ........... 514/594 |

FOREIGN PATENT DOCUMENTS

| | | |
|---|---|---|
| 0071279 | 2/1983 | European Pat. Off. |
| 0088343 | 9/1983 | European Pat. Off. |
| 0154508 | 9/1985 | European Pat. Off. |
| 0226642 | 7/1987 | European Pat. Off. |
| 2726684 | 1/1979 | Fed. Rep. of Germany. |
| 3607298 | 9/1986 | Fed. Rep. of Germany. |
| 2023152 | 8/1987 | Fed. Rep. of Germany. |
| 59-106454 | 6/1984 | Japan. |
| 61-277660 | 12/1986 | Japan. |
| 1168658 | 7/1989 | Japan. |

OTHER PUBLICATIONS

C. R. Acad. Sc. Paris, T. 258 (Jun. 22, 1964), Groupe 8. 6175-6177, Le Guyander et al., "Reduction Electrochimique, A Potentiel Controle, De Quelques Nitrobenzenes Orthosubstitues".

Veigand-Hilgetat, "Methods of Experiment in Organic Chemistry", Khimia Publishers, Moscow, 1958, p. 520.

*Primary Examiner*—Alan Siegel
*Attorney, Agent, or Firm*—Stevens, Davis, Miller & Mosher

[57] ABSTRACT

The present invention relates to a novel benzoylurea derivative represented by the formula;

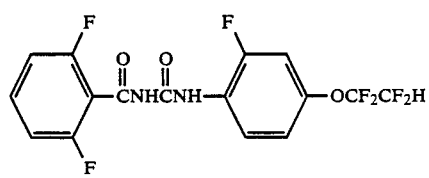

its production; and insecticides, ovicides for insects and chemosterilants for insects containing it as an active ingredient.

The benzoylurea derivative is produced by reacting a benzamide compound represented by the formula,

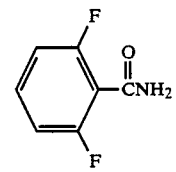

with an isocyanate compound represented by the formula,

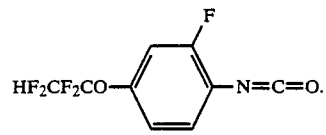

4 Claims, No Drawings

BENZOYLUREA DERIVATIVE AND ITS PRODUCTION AND USE

CROSS-REFERENCE TO RELATED APPLICATIONS

This is a continuation-in-part of application Ser. No. 150,990, filed on Feb. 1, 1988 now U.S. Pat. No. 4,904,696.

The present invention relates to a novel benzoylurea derivative represented by the formula (I);

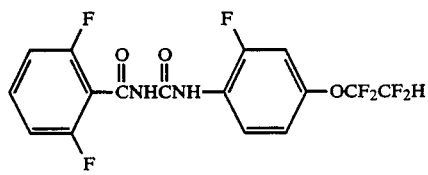

its production; and insecticides, ovicides for insects and chemosterilants for insects containing it as an active ingredient.

The present inventors have made many studies to develop excellent insecticides, and as a result, have found that the benzoylurea derivative represented by the foregoing formula (I) (hereinafter referred to as present compound) has excellent insecticidal activity, particularly a very high insecticidal activity against the eggs, larvae or nymphs of insect pests, and has an excellent sterile activity for insects, and also so that it can be produced relatively cheaply. The present inventors thus attained to the present invention.

Hitherto, benzoylurea compounds belonging to a certain kind have been known to have an insecticidal activity [U.S. Pat. Nos. 3,933,908, 4,139,636, 4,170,657 and 4,457,943; E.P. Nos. 71,279A1 and 226,642A1; Japanese Patent Publication Kokai (Laid-open) No. 106454/1984], and some of them are already on the market. Recently, however, it has been found the present compound has an insecticidal, an ovicidal and a sterile activities superior to those of these compounds.

Specific examples of insect pests against which the present compound is particularly efficacious will be given below: Insect pests belonging to Lepidoptera such as diamond-back moth (*Plutella xylostella*), rice stem borer (*Chilo suppressalis*), armyworms and cutworms (Noctuidae), small white butterfly (*Pieris rapae curcivora*), casemaking clothes moth (*Tinea pellionella*), webbing clothes moth (*Tineola bisselliella*), etc.; insect pests belonging to Diptera such as house mosquitoes (*Culex* spp.) [e.g. *Culex pipiens pallens*], Anopheline mosquitoes (*Anopheles* spp.), Aedes mosquitoes (*Aedes* spp.), chironomid midges, houseflies (Muscidae), blow flies (Calliphoridae), flesh flies (Sarcophagidae), tabanid flies (Tabanidae), black flies, etc.; insect pests belonging to Dictyoptera such as German cockroach (*Blattella germanica*), smokybrown cockroach (*Periplaneta fuliginosa*), brown cockroach (*Periplaneta brunnea*), American cockroach (*Periplaneta americana*), etc.; and other insect pests belonging to Coleoptera or Hymenoptera.

The present compounds exhibit a high controlling activity against the above-mentioned insect pests in each stage as follows:

Against the eggs of the insect pests, the present compounds exhibit a high ovicidal activity. Against the larvae and nymphs of the insect pests, they exhibit a high controlling activity by inhibiting the ecdysis. Against the adults of the insect pests, they show a high sterile activity (the activity to inhibit the oviposition) or a high trans-ovarial activity (the activity to inhibit the hatching).

The present compounds exhibit the above-mentioned activities against the larvae, nymphs and adults of the insect pests not only by making contact with the insects but also by being ingested by the insects.

Also, the present compound is low in toxicity to warm-blooded animals so that it can be orally administered by mixing with feeds for animals, to domestic animals such as cattle, pigs, horses, sheep, goats, chickens, etc. As a result, the present compound is excreted from animals as undecomposed, so that the eggs and the larvae of insect pests living in the excrement of domestic animals [e.g. housefly (*Musca domestica*), false stablefly (*Muscina stabulans*), little housefly (*Fannia canicularis*), blow flies (Calliphoridae), flesh flies (Sarcophagidae), sepsid flies (Sepsidae)], can be exterminated.

The present compound represented by the formula (I) can be produced by the following methods.

Method A

A method comprising reacting a benzoylisocyanate compound represented by the formula (II),

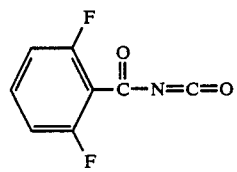

with an aniline compound represented by the formula (III),

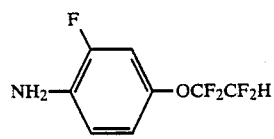

Method B

A method comprising reacting a benzamide compound represented by the formula (IV),

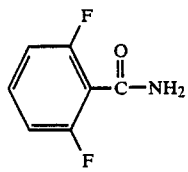

with an isocyanate compound represented by the formula (V),

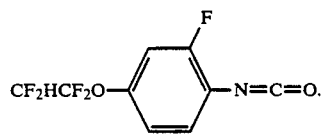

In the foregoing Methods A and B, the reaction is usually carried out in the presence of an inert solvent. The solvent usable includes for example aromatic hydrocarbons (e.g. benzene, toluene, xylene), halogenated hydrocarbons (e.g. chlorobenzene, carbon tetrachloride, chloroform, methylene chloride, 1,2dichloroethane), ethers (e.g. diethyl ether, tetrahydrofuran, dioxane), ketones (e.g. acetone, methyl ethyl ketone, methyl isobutyl ketone), dimethyl sulfoxide, dimethylformamide, nitromethane and mixtures thereof.

In Methods A and B, the reaction can generally be carried out under normal pressure, and usually for a period of 1 to 50 hours. The amounts of the starting compounds are generally in an equimolar ratio, but one of the starting compounds may be used in excess.

In Methods A and B, the reaction temperature is not particularly limited, but it is in a range of generally from 0° to 80° C., usually from room temperature (ca. 25° C.) to 60° C. for Method A, and generally from room temperature to 160° C., usually from 80° to 130° C. for Method B.

The present compound thus obtained can be purified if necessary by means such as column chromatography, recrystallization, etc.

In the production of the present invention, the aniline compound represented by the formula (III), a starting compound is a novel compound, and it can be produced, for example, by the methods described below:

Synthetic method 1

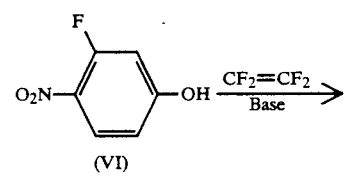

(VI)

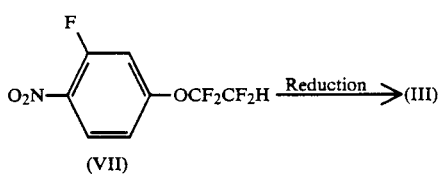

(VII)

Synthetic method 2

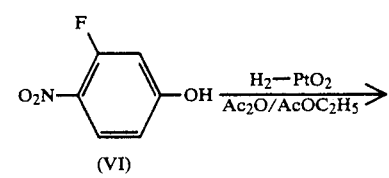

(VI)

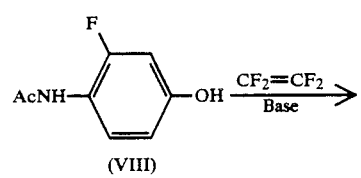

(VIII)

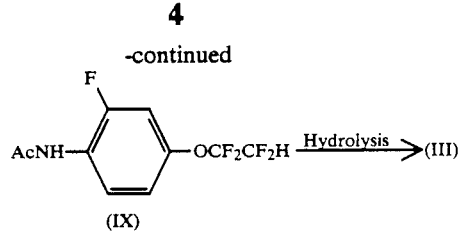

(IX)

Synthetic method 3:

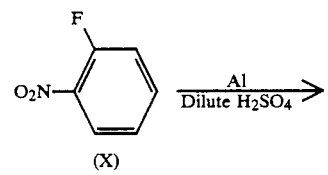

(X)

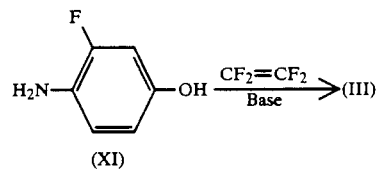

(XI)

In Synthetic method 1, the aniline compound (III) is obtained by reacting 3-fluoro-4-nitrophenol (VI) with tetrafluoroethylene in the presence of a base and reducing the resulting compound (VII), for example, with iron in the presence of an acid or catalytically reducing the compound (VII) with hydrogen in the presence of platinum dioxide.

In Synthetic method 2, the aniline compound (III) is obtained by catalytically reducing 3-fluoro-4-nitrophenol (VI) with hydrogen in the presence of acetic anhydride, ethyl acetate and platinum dioxide, reacting the resulting compound (VIII) with tetrafluoroethylene in the presence of a base to obtain a compound (IX) and hydrolyzing the acetylamino group of the compound (IX) by the usual method.

In Synthetic method 3, the aniline compound (III) is obtained by reacting cheap and easily available o-fluoronitrobenzene with metallic aluminum in the presence of a dilute sulfuric acid to obtain 3-fluoro-4aminophenol (XI) in a high yield, and reacting the compound (XI) with tetrafluoroethylene in the presence of a basic catalyst.

This reaction is usually carried out under the following condition. Metallic aluminum used to produce the aminophenol (XI) may have any form of a powder and a chip, but a powder is preferably used. The concentration of the sulfuric acid is from 1 to 50%, preferably about 10%, and the reaction temperature is from 50° to 100° C., preferably from 90° to 95° C.

In carrying out this reaction, the amount of sulfuric acid used is from 1 to 3 times by mole, preferably about 1.5 times by mole based on 1 mole of o-fluoronitrobenzene. The amount of metallic aluminum is from 1 to 3 times by mole, preferably about 1.7 times by mole based on the same.

The basic catalyst used in reacting the aminophenol (XI) with tetrafluoroethylene includes for example caustic alkalis (e.g. caustic potash), alkali carbonates (e.g. potassium carbonate), etc., but caustic potash is preferably used.

The reaction is usually carried out in an inert solvent, and the solvent includes for example dimethylformamide, mixed solvents of dimethylformamide and other inert solvents (e.g. toluene, acetonitrile, dioxane), etc., but dimethylformamide is preferably used. The reaction temperature is from 30° to 150° C., preferably from 70° to 100° C.

In carrying out this reaction, the amount of tetrafluoroethylene used is not less than an equimolar amount based on 1 mole of the aminophenol (XI). The reaction product thus obtained can easily be purified if necessary by distillation, etc.

Said aniline compound (III) can be converted to an isocyanate compound represented by the formula (V) by reacting it with phosgene according to the usual method, and usually, this reaction is carried out under the following condition. The amount of phosgene used in this reaction is usually from 1 to 5 times by mole based on 1 mole of the aniline compound (III). In this reaction, an inert solvent is usually used, and normally, it includes for example hydrocarbons (e.g. hexane, heptane, benzene, toluene), halogenated hydrocarbons (e.g. dichloromethane, chloroform, 1,2-dichloroethane, chlorobenzene) and mixtures of two or more of them. This reaction well proceeds at a temperature ranging from room temperature to the boiling point of the solvent. The reaction product thus obtained can easily be purified if necessary by distillation, etc.

When the present compounds are used as an active ingredient for insecticides, ovicides and/or chemosterilants, they are usually formulated into oil sprays, emulsifiable concentrates, wettable powders, flowable concentrates, granules, dusts, aerosols, foggings, poisonous baits, etc. by mixing with solid carriers, liquid carriers, gaseous carriers or baits and if necessary, adding surface active agents and other auxiliaries for formulation.

These preparations usually contain the present compounds as an active ingredient in an amount of from 0.01 to 95% by weight.

The solid carriers used in the formulation include for example fine powders or granules of clays (e.g. kaolin clay, diatomaceous earth, synthetic hydrated silicon dioxide, bentonite, Fubasami clay, terra alba), talcs, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. The liquid carriers include for example water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carriers, i.e. a propellant, include for example freon gas, butane gas, LPG (liquefied petroleum gas), dimethyl ether, carbon dioxide gas, etc.

The surface active agents include for example alkyl sulfates, alkylsulfonates, alkylarylsulfonates, alkyl aryl ethers and their polyoxyethylenized products, polyethylene glycol ethers, polyhydric alcohol esters, sugar alcohol derivatives, etc.

The auxiliaries for formulation such as fixing agents, dispersing agents, etc. include for example casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agents include for example PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The base of the poisonous baits includes for example components (e.g. grain powders, vegetable essential oils, saccharides, crystalline celluloses), antioxidants (e.g. dibutylhydroxytoluene, nordihydroguaiaretic acid), preservatives (e.g. dehydroacetic acid), attractants (e.g. cheese perfume, onion perfume, peanut oil), etc. Further, red pepper powders etc. also are included as an agent for preventing children from eating by mistake.

The preparations thus obtained are used as they are or diluted with water, etc. Further, they may be used mixed with other insecticides, nematocides, acaricides, soil-pest controlling agents, fungicides, herbicides, plant growth regulators, synergists, fertilizers, soil improvers, feeds for animals etc., or may be used simultaneously with these chemicals without mixing.

When the present compounds are used as agricultural insecticides, ovicides and/or chemosterilants, their dosage rate is usually from 0.5 to 500 g/10 ares. When the emulsifiable concentrates, wettable powders, flowable concentrates, etc. are used diluted with water, the application concentration of the active ingredient is 0.1 to 1000 ppm. The granules, dusts, etc. are used as they are without being diluted. When the present compounds are used as household and public hygienic insecticides, ovicides and/or chemosterilants, the emulsifiable concentrates, wettable powders, flowable concentrates, etc. are applied diluted with water to 0.1 to 1000 ppm, and the oil sprays, aerosols, foggings, poisonous baits, etc. are applied as they are.

Although any of these dosage rate and application concentration depends on the type of preparations, when, where and how these preparations are applied, the kind of pests, the degree of damage, etc., they may be increased or decreased independently of the ranges explained above.

The present compound will be illustrated in more detail with reference to the following production examples, formulation examples and test examples, but the present invention is not limited to these examples.

PRODUCTION EXAMPLE 1

0.15 Gram of 2-fluoro-4-(1,1,2,2-tetrafluoroethoxy)aniline was dissolved in 5 ml of toluene, and to the resulting solution was added dropwise a solution of 0.12 g of 2,6-difluorobenzoylisocyanate in 3 ml of toluene with stirring and ice-cooling. After completion of the addition, the reaction solution was stirred overnight at room temperature, and 5 ml of n-hexane was added. The precipitated crystals were filtered off and dried to obtain 0.19 g of N-2,6-difluorobenzoyl-N'-[2-fluoro-4(1,1,2,2-tetrafluoroethoxy)phenyl]urea as white crystals.

Yield: 70% m.p.: 173°–174° C.

PRODUCTION EXAMPLE 2

0.16 Gram of 2,6-difluorobenzamide, 0.25 g of 2-fluoro-4-(1,1,2,2-tetrafluoroethoxy)phenylisocyanate and 20 ml of xylene were added to a reactor and stirred under reflux for 24 hours. The reaction solution was cooled and concentrated to obtain a crude product. This crude product was subjected to chromatography on silica gel to obtain 0.24 g of N-2,6-difluorobenzoyl-N'-[2-fluoro-4-(1,1,2,2-tetrafluoroethoxy)phenyl]urea as white crystals.

Yield: 60%
m.p.: 172°–173° C.

PRODUCTION EXAMPLE 3

After dissolving 1.15 g of 3-fluofo-4-nitrophenol in 10 ml of dioxane, the resulting solution was violently stirred at about 60° C. for 15 minutes under the stream of a tetrafluoroethylene gas in large excess of said phenol. After quickly adding 0.04 g of potassium hydroxide, the solution was violently stirred for 2 hours under the same condition. The reaction solution was cooled, and after adding water, extracted with two 100-ml portions of diethyl ether. The ether layers were combined, dried and concentrated to obtain a yellow oily product as a residue. This oily product was subjected to chromatography on silica gel to obtain 0.20 g of 2-fluoro-4-(1,1,2,2-tetrafluoroethoxy)nitrobenzene.

Yield: 10.6%
$^{19}$F-NMR (CDCl$_3$CF$_3$COOH): δ(ppm) −10(2F, s), −33(1F, s), −57(2F, d, $J_{F-H}$=54 Hz)

0.20 Gram of 2-fluoro-4-(1,1,2,2-tetrafluoroethoxy)nitrobenzene, 0.03 g of platinum dioxide and 5 ml of ethyl acetate were added to a reactor, and the atmosphere in the reactor was replaced by a hydrogen stream with stirring. Stirring was then continued at room temperature for 2 hours while introducing a hydrogen gas. Thereafter, the reaction solution was filtered off, and the filtrate was concentrated to obtain 0.15 g of 2-fluoro-4-(1,1,2,2-tetrafluoethoxy)aniline.

Yield: 85%
$n_D^{25.5}$: 1.446
$^{19}$F-NMR (CDCl$_3$/CF$_3$COOH): δ(ppm) −10.5(2F, s), −52.5(1F, s), −57.5(2F, d, $J_{F-H}$=53 Hz)

PRODUCTION EXAMPLE 4

5.0- Grams of 3-fluoro-4-nitrophenol, 3.57 g of acetic anhydride, 0.72 g of platinum dioxide and 50 ml of ethyl acetate were added to a reactor, and the atmosphere in the reactor was replaced by a hydrogen stream with stirring. Stirring was then continued at room temperature for 6 hours while introducing a hydrogen gas. Thereafter, the reaction solution was filtered off, and the filtrate was washed with two 50-ml portions of a 5% aqueous sodium hydrogencarbonate solution, dried and concentrated. The residue was subjected to chromatography on silica gel to obtain 4.47 g of 4-acetylamino-3fluorophenol.

Yield: 83%
m.p.: 124° C.

0.93 Gram of 4-acetylamino-3-fluorophenol, 0.15 g of potassium carbonate and 15 ml of dimethylformamide were added to a reactor and stirred for 20 minutes at an oil bath temperature of from 60° to 70° C. Thereafter, this solution was violently stirred at the same temperature for 1 hour under the stream of a tetrafluoroethylene gas in excess of said phenol. The reaction solution was cooled and after adding water, extracted with two 100-ml portions of diethyl ether. The ether layers were combined, washed with water, dried and concentrated to obtain a crude product. This crude product was subjected to chromatography on silica gel to obtain 1.46 g of 4-acetylamino-3-fluoro-1-(1,1,2,2- c tetrafluoroethoxy)benzene.

Yield: 98%
$^{19}$F-NMR (CDCl$_3$/CF$_3$COOH): δ(ppm) −10(2F, s), −47(1F, s), −57(2F, d $J_{F-H}$=53 Hz)

0.60 Gram of 4-acetylamino-3-fluoro-1-(1,1,2,2tetrafluoroethoxy)benzene and 10 ml of a 20% aqueous hydrochloric acid were added to a reactor and stirred under reflux for 2 hours. After cooling the reaction solution, a 5% aqueous sodium hydrogencarbonate solution was added to make the solution weakly alkaline. The reaction solution was then extracted with two 100-ml portions of diethyl ether. The ether layers were combined, dried and concentrated to obtain a yellow oily product as a residue. This oily product was subjected to chromatography on silica gel to obtain 0.40 g of 2-fluoro-4-(1,1,2,2-tetrafluoroethoxy)aniline.

Yield: 81%

PRODUCTION EXAMPLE 5

2.03 Grams of o-fluoronitrobenzene, 0.70 g of aluminum powder, 43 ml of water and 4.4 g of conc. sulfuric acid were added to a reactor and stirred at an inner temperature of from 90° to 95° C. for 40 minutes. After cooling the reaction solution, a 5% aqueous sodium hydrogencarbonate solution was added to make the reaction solution weakly alkaline. The reaction solution was then extracted with three 100-ml portions of diethyl ether. The ether layers were combined, dried and concentrated to obtain a crude product. This crude product was subjected to chromatography on silica gel to obtain 1.58 g of 3-fluoro-4-aminophenol.

Yield: 86%
m.p.: 137°–138° C.

0.70 Gram of 3-fluoro-4-aminophenol, 0.06 g of potassium hydroxide and 10 ml of dimethylformamide were added to a reactor and stirred for 20 minutes at an oil bath temperature of from 60° to 70° C. This solution was then violently stirred at the same temperature for 2 hours under the stream of a tetrafluoroethylene gas in excess of said phenol. The reaction solution was cooled and after adding water, extracted with two 150-ml portions of diethyl ether. The ether layers were combined, washed with water, dried and concentrated to obtain a crude product. This crude product was subjected to chromatography on silica gel to obtain 1.00 g of 2-fluoro-4-(1,1,2,2-tetrafluoroethoxy)aniline.

Yield: 80%

Formulation examples will be shown. Parts in the examples are by weight.

FORMULATION EXAMPLE 1

Ten parts of the present compound, 14 parts of polyoxyethylene styrylphenyl ether, 6 parts of calcium dodecylbenzenesulfonate, 35 parts of xylene and 35 parts of dimethylformamide are well mixed to obtain an emulsifiable concentrate.

FORMULATION EXAMPLE 2

Twenty parts of the present compound, 10 parts of fenitrothion (O,O-dimethyl O-4-nitro-m-tolyl phosphorothioate), 3 parts of calcium lignosulfonate, 2 parts of sodium lauryl sulfate and 65 parts of synthetic hydrated silicon dioxide are well pulverized and mixed to obtain a wettable powder.

FORMULATION EXAMPLE 3

One part of the present compound, 2 parts of carbaryl (1-naphthyl N-methylcarbamate), 87 parts of kaolin clay and 10 parts of talc are well pulverized and mixed to obtain a dust.

FORMULATION EXAMPLE 4

Five parts of the present compound, 1 part of synthetic hydrated silicon dioxide, 2 parts of calcium ligno-sulfonate, 30 parts of bentonite and 62 parts of kaolin clay are well pulverized and mixed. The resulting mixture is well kneaded with water, granulated and dried to obtain a granule.

FORMULATION EXAMPLE 5

Twenty parts of the present compound, 3 parts of a sodium naphthalenesulfonate/formalin condensate and 75 parts of water are well pulverized and mixed. Thereafter, two parts of methyl cellulose, a thickening agent, is added to the resulting mixture and mixed to obtain a flowable concentrate.

FORMULATION EXAMPLE 6

30 Milligrams of the present compound is dissolved in 0.5 ml of acetone, and the resulting solution is uniformly applied onto a piece (3 g) of solid animal food (solid food for rearing and breeding CE-2, a registered trademark of Clea Japan Inc.). Acetone is removed by air-drying to obtain a poisonous bait.

Test examples will be shown. Compounds used as a control are shown by compound symbols in Table 1.

TABLE 1

| Compound symbol | Structural formula | Remarks |
| --- | --- | --- |
| (A) | 2,6-difluoro-C$_6$H$_3$-CONHCONH-C$_6$H$_4$-Cl (para) | Diflubenzuron (compound described in U.S. Pat. No. 3,933,908). |
| (B) | 2-Cl-C$_6$H$_4$-CONHCONH-C$_6$H$_4$-OCF$_3$ (para) | Triflumuron (compound described in U.S. Pat. No. 4,139,636). |
| (C) | 2,6-difluoro-C$_6$H$_3$-CONHCONH-(2,5-Cl$_2$-4-F-C$_6$H$_2$) | Teflubenzuron (compound described in U.S. Pat. No. 4,457,943). |
| (D) | 2,6-difluoro-C$_6$H$_3$-CONHCONH-(3,5-Cl$_2$-4-OCF$_2$CHF$_2$-C$_6$H$_2$) | Hexafluron (compound No. 1 described in E.P. No. 71279A1). |
| (E) | 2,6-difluoro-C$_6$H$_3$-CONHCONH-(3-Cl-4-OCF$_2$CF$_2$H-C$_6$H$_3$) | Compound unknown to the literatures. m.p. 158.7° C. |
| (F) | 2,6-difluoro-C$_6$H$_3$-CONHCONH-(3-Cl-4-OCF$_2$CHFCl-C$_6$H$_3$) | Compound No. 18 described in U.S. Pat. No. 4,139,636. |

TABLE 1-continued

| Compound symbol | Structural formula | Remarks |
|---|---|---|
| (G) | 2,6-difluorobenzoyl-NHC(O)NH-(3-chloro-4-trifluoromethoxyphenyl) | Compound No. 29 described in U.S. Pat. No. 4,139,636. |
| (H) | 2,6-difluorobenzoyl-NHC(O)NH-(2-fluoro-4-chlorophenyl) | Compound No. 1 described in Japanese Patetn Publication Kokai (Laid-open) No. 106454/ 1984. |
| (I) | $CH_3S$-C(CH_3)=N-OC(O)NHCH_3 (Methomyl structure) | Methomyl |
| (J) | 2,6-difluorobenzoyl-NHC(O)NH-(4-trifluoromethoxyphenyl) | Compound No. 61 described in U.S. Pat. No. 4,139,636. |
| (K) | 2,6-difluorobenzoyl-NHC(O)NH-(2-chloro-4-trifluoromethoxyphenyl) | Compound described in E.P. No. 226,642A1 as comparative one. |
| (L) | 2,6-difluorobenzoyl-NHC(O)NH-(4-OCF$_2$CF$_2$H-phenyl) | Compound No. 6 described in U.S. Pat. No. 4,170,657. |
| (M) | 2,6-difluorobenzoyl-NHC(O)NH-(2-fluoro-4-trifluoromethoxyphenyl) | Compound No. 8 described in E.P. No. 226,642A1. |
| (N) | 2,6-difluorobenzoyl-NHC(O)NH-(3-fluoro-4-OCF$_2$CF$_2$H-phenyl) | Compound unknown to the literatures. m.p. 217.9° C. |
| (O) | 2,6-difluorobenzoyl-NHC(O)NH-(2,3-dichloro-4-OCF$_2$CF$_2$H-phenyl) | Compound No. 48 described in E.P. No. 71,279A1. |

TABLE 1-continued

| Compound symbol | Structural formula | Remarks |
|---|---|---|
| (P) | F-C6H3(F)-CNHCNH-C6H3(Cl)-OCF2CF2H (2,6-difluorobenzoyl; 3-chloro-4-(OCF2CF2H)phenyl urea) | Compound unknown to the literatures. m.p. 185.9° C. |

TEST EXAMPLE 1: Test for controlling larvae of tobacco cutworm (*Spodoptera litura*)

Two milliliters each of the 200,000-fold aqueous dilute solutions (corresponding to 0.5 ppm) of emulsifiable concentrates prepared from the present compound and comparative compounds according to Formulation example 1 were applied onto 13 g of artificial diet for tobacco cutworm (*Spodoptera litura*), and the diet was put in a polyethylene cup of 11 cm in diameter. Then, ten fourth-instar larvae of tobacco cutworm were liberated in the cup. After six days, the dead and alive were examined to obtain mortality (two replications).

The results are shown in Table 2.

TABLE 2

| Test compound | Mortality (%) |
|---|---|
| Present compound | 100 |
| (A) | 5 |
| (B) | 0 |
| (C) | 20 |
| (D) | 5 |
| (E) | 5 |
| (F) | 20 |
| (G) | 30 |
| (H) | 10 |
| (I) | 0 |
| (J) | 0 |
| (K) | 25 |
| (L) | 0 |
| (M) | 50 |
| (N) | 0 |
| (O) | 0 |
| (P) | 5 |
| No treatment | 5 |

TEST EXAMPLE 2: Test for controlling larvae of rice stem borer (*Chilo suppressalis*)

One milliliter each of the 67,000-fold aqueous dilute solutions (corresponding to 1.5 ppm) of emulsifiable concentrates prepared from the present compound and comparative compounds according to Formulation example 1 was applied onto 5 g of artificial diet for rice stem borer (*Chilo suppressalis*) which had been previously prepared in a polyethylene cup of 5.5 cm in diameter. Then, ten 10-day old larvae of rice stem borer were liberated in the cup. After eight days, the dead and alive were examined to obtain mortality (two replications). The results are shown in Table 3.

TABLE 3

| Test compound | Mortality (%) |
|---|---|
| Present compound | 100 |
| (A) | 30 |
| (B) | 5 |
| (C) | 45 |
| (D) | 40 |
| (E) | 10 |
| (F) | 15 |
| (G) | 0 |
| (H) | 35 |
| (I) | 5 |
| (J) | 5 |
| (K) | 40 |
| (L) | 30 |
| (M) | 55 |
| (N) | 10 |
| (O) | 0 |
| (P) | 5 |
| No treatment | 5 |

TEST EXAMPLE 3: Test for controlling nymphs of German cockroach (*Blattella germanica*)

Each of the present compound and comparative compounds was diluted with acetone and uniformly applied onto the filter paper (10 cm × 5 cm, area: 50 cm$^2$) so that its dosage rate was 1 mg/m$^2$. After acetone had been evaporated off, this treated filter paper was bent into wave and put into a polyethylene cup (diameter: 12 cm, height: 7 cm) as a shelter for cockroaches. Then 100 first-instar nymphs of German cockroach (*Blattella germanica*) were liberated in the polyethylene cup with water and diet.

After 2 weeks, the dead and alive of nymphs were examined to obtain mortality.

The results are shown in Table 4.

TABLE 4

| Test compound | Mortality (%) |
|---|---|
| Present compound | 100 |
| (A) | 13 |
| (B) | 24 |
| (C) | 2 |
| (D) | 29 |
| (E) | 10 |
| (F) | 28 |
| (G) | 21 |
| (H) | 13 |
| (J) | 4 |
| (K) | 11 |
| (L) | 23 |
| (M) | 46 |
| (N) | 33 |
| (O) | 19 |
| (P) | 16 |
| No treatment | 1 |

TEST EXAMPLE 4: Test for controlling larvae of diamond-back moth (*Pluttella xylostella*)

The emulsifiable concentrates containing each of the present compound and comparative compounds were prepared according to Formulation Example 1. They were each diluted with water to 1,000,000-volume aqueous solutions (active ingredient concentration: 0.1 ppm). And 40 ml of each of the solution thus obtained were sprayed onto the leaves of potted cabbage plant. After drying, 10 third-instar larvae of diamond-back moth (*Plutella xylostella*) of a field strain were released on the treated leaves. After five days, the dead and alive were examined to obtain the mortality (two replications).

The results are shown in Table 5.

TABLE 5

| Test compound | Mortality (%) |
|---|---|
| Present compound | 100 |
| (A) | 5 |
| (B) | 10 |
| (C) | 15 |
| (D) | 25 |
| (E) | 25 |
| (F) | 20 |
| (G) | 25 |
| (H) | 5 |
| (J) | 10 |
| (K) | 40 |
| (L) | 15 |
| (M) | 50 |
| (N) | 35 |
| (O) | 5 |
| (P) | 15 |
| No treatment | 5 |

TEST EXAMPLE 5: Test for controlling eggs of diamond-back moth (*Pluttella xylostella*)

The emulsifiable concentrates of each of the following present compound and comparative compounds prepared according to Formulation Example 1 were diluted 80,000 times with water (corresponding to 1.25 ppm). Two pieces of germinated Japanese radish which had been sowed 5 or 6 days before were dipped for 30 seconds in the aqueous dilute solution. After air-drying for about 1 hour, these germinated radish were put in a cage wherein a large number of adult diamond-back moth (*Plutella xylostella*) (field-strain) of an age of 1-3 days after the emergence were released, and they were allowed to lay eggs. When the number of eggs per germinated radish reached 100 to 150, the radish were taken out of the cage and each two pieces thereof were put in a polyethylene cup of 5.5 cm in diameter. After 5 days, the number of hatching was counted to obtain inhibition of hatching. This test was repeated twice.

The inhibition of hatching was indicated in the following four grades;
A: 100%
B: 90-99%
C: 80-89%
D: 79% or less The results are shown in Table 6.

TABLE 6

| Test compound | Inhibition of hatching |
|---|---|
| Present compound | A |
| (A) | D |
| (B) | D |
| (C) | D |
| (D) | D |
| (E) | D |
| (F) | D |
| (G) | D |
| (H) | D |
| (J) | D |
| (K) | D |
| (L) | D |
| (M) | C |
| (N) | D |
| (O) | D |
| (P) | D |
| No treatment | D |

TEST EXAMPLE 6: Test for sterilizing adults of German cockroach (*Blattella germanica*)

Each of the present compound and comparative compounds was diluted with acetone and uniformly applied onto a filter paper (10 cm×5 cm, area: 50 cm$^2$) so that its dosage rate was 10 mg/m$^2$. After acetone had been evaporated off, this treated filter paper was bent into wave and put into a polyethylene cup (diameter: 12 cm, height: 7 cm) as a shelter for cockroaches. Then, 10 virgin female and 5 male adult German cockroaches (*Blattella germanica*) were liberated in the polyethylene cup with water and diet.

After 1 month, the number of normal hatching oothecae of adult female was examined to obtain percentage of sterilization (two replications).

The results are shown in Table 7.

TABLE 7

| Test compound | Sterilization (%) |
|---|---|
| Present compound | 100 |
| (A) | 25 |
| (B) | 10 |
| (C) | 40 |
| (D) | 35 |
| (E) | 15 |
| (F) | 20 |
| (G) | 10 |
| (H) | 20 |
| (J) | 0 |
| (K) | 30 |
| (L) | 30 |
| (M) | 45 |
| (N) | 15 |
| (O) | 5 |
| (P) | 10 |
| No treatment | 0 |

TEST EXAMPLE 7: Test for controlling eggs of housefly (*Musca domestica*)

Fifty eggs of housefly (*Musca domestica*) (fieldstrain) were put on a central hole (inner diameter: 15 mm) of a micro slide glass (76 mm×26 mm) within 2 hours from the oviposition. The emulsifiable concentrates of each of the following present compound and comparative compounds were prepared according to the Formulation Example 1. Thereafter it was diluted 1,000 times with water so that the active ingredient concentration corresponds to 100 ppm. Then 25 μl of each of the solution were dropped on the eggs. The dipped eggs in the hole of the slide glass were kept in a humid condition (95-100% RH). After 24 hours, the number of hatching eggs was counted to obtain an inhibition of hatching (two replications).

The results are shown in Table 8.

TABLE 8

| Test compound | Inhibition of hatching (%) |
| --- | --- |
| Present compound | 100 |
| (A) | 14 |
| (B) | 10 |
| (C) | 16 |
| (D) | 18 |
| (E) | 24 |
| (F) | 8 |
| (G) | 16 |
| (H) | 6 |
| (J) | 20 |
| (K) | 24 |
| (L) | 28 |
| (M) | 48 |
| (N) | 12 |
| (O) | 6 |
| (P) | 14 |
| No treatment | 8 |

What is claimed is:

1. An ovicidal composition for insects which comprises an ovicidally effective amount of a benzoylurea derivative of the formula:

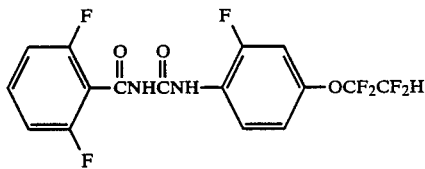

and an inert carrier.

2. A chemosterilant composition for insects which comprises a sterilely effective amount of a benzoylurea derivative of the formula:

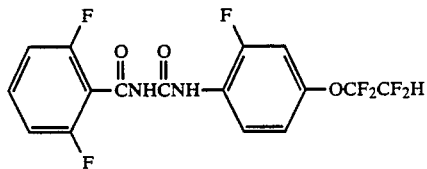

and an inert carrier.

3. A method for destroying eggs of insects which comprises applying an ovicidally effective amount of a benzoylurea derivative of the formula:

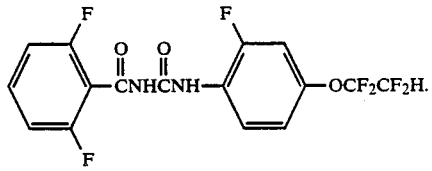

4. A method for sterilizing adults of insects which comprises applying an sterilely effective amount of a benzoylurea derivative of the formula:

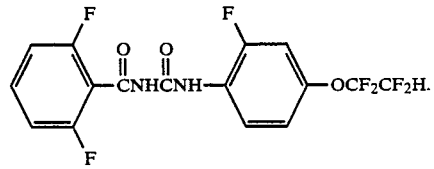

* * * * *